United States Patent
Nagase et al.

(10) Patent No.: US 6,756,509 B2
(45) Date of Patent: Jun. 29, 2004

(54) METHOD FOR PURIFYING CRUDE 2,6-NAPHTHALENEDICARBOXYLIC ACID

(75) Inventors: Yoshiyuki Nagase, Kobe (JP); Koji Yamamoto, Kobe (JP); Takeharu Tanaka, Kobe (JP); Maki Hamaguchi, Kobe (JP)

(73) Assignee: Kobe Steel, Ltd., Kobe (JP)

( * ) Notice: Subject to any disclaimer, the term of this patent is extended or adjusted under 35 U.S.C. 154(b) by 135 days.

(21) Appl. No.: 10/193,231

(22) Filed: Jul. 12, 2002

(65) Prior Publication Data

US 2003/0088121 A1 May 8, 2003

(30) Foreign Application Priority Data

Jul. 13, 2001 (JP) .................................... 2001-214142

(51) Int. Cl.[7] .................... C07C 51/42; C07C 63/48; C07C 51/16
(52) U.S. Cl. .............. 562/485; 562/486; 562/488; 562/487; 562/417
(58) Field of Search .................... 562/417, 416, 562/487, 488, 486, 485

(56) References Cited

U.S. PATENT DOCUMENTS 3,671,578 A * 6/1972 Ogata et al. ............ 562/488
5,256,817 A * 10/1993 Sikkenga et al. ........ 562/487

OTHER PUBLICATIONS

Derwent Publications, AN 1997–359113, XP–002215550, JP 09–151162, Jun. 10, 1997.

* cited by examiner

Primary Examiner—Alan L. Rotman
Assistant Examiner—Taylor V Oh
(74) Attorney, Agent, or Firm—Oblon, Spivak, McClelland, Maier & Neustadt, P.C.

(57) ABSTRACT

A method for purifying crude 2,6-naphthalenedicarboxylic acid includes a reduction step of reducing crude 2,6-naphthalenedicarboxylic acid containing 6-formyl-2-naphthoic acid with hydrogen and a cleaning step of cleaning the reduction product with alcohol. Preferably, in the reduction step, the crude 2,6-naphthalenedicarboxylic acid and the hydrogen is brought into contact with a hydrogenation catalyst in a liquid phase, and particularly in water. The method makes the purification process less complex and makes it possible to produce high-purity 2,6-naphthalenedicarboxylic acid without damaging equipment or increasing cost.

20 Claims, 3 Drawing Sheets

METHOD FOR PURIFYING CRUDE 2,6-NAPHTHALENEDICARBOXYLIC ACID

BACKGROUND OF THE INVENTION

1. Field of the Invention

The present invention relates to methods for producing, from crude naphthalenedicarboxylic acid containing 6-formyl-2-naphthoic acid, high-purity 2,6-naphthalenedicarboxylic acid which is advantageously used as a material in engineering plastics, such as polyethylene naphthalate and polybutylene naphthalate. In particular, the present invention relates to a method for purifying crude 2,6-naphthalenedicarboxylic acid to obtain high-purity 2,6-naphthalenedicarboxylic acid. The method prevents corrosion of equipment and allows aftertreatment to be simple.

2. Description of the Related Art

Naphthalenedicarboxylic acid, and more particularly, 2,6-naphthalenedicarboxylic acid (2,6-NDA) is used as an important material in engineering plastics such as polyethylene naphthalate (PEN) and polybutylene naphthalate (PBN).

As shown in the following formula, 2,6-NDA is produced by oxidizing 2,6-dimethylnaphthalene (2,6-DMN) in a gas phase or a liquid phase.

Formula

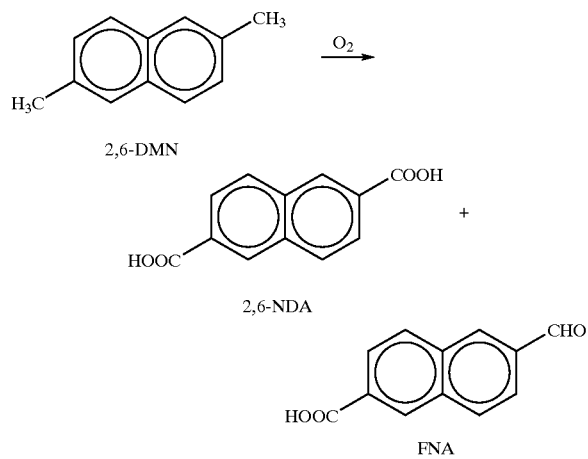

In a process using this oxidization reaction, however, the methyl group is not completely oxidized, and consequently 6-formyl-2-naphthoic acid (FNA) is produced as a by-product. When polyester, such as polyethylene naphthalate or polybutylene naphthalate, is produced from 2,6-NDA by polycondensation, FNA degrades the degree of polymerization and colors the polyester. Therefore, 2,6-NDA used for polyester must be of high purity, and specifically, it must not contain the impurity, that is, FNA.

Since 2,6-NDA and FNA have similar physical properties, such as boiling point and melting point, they cannot be separated by distillation or crystallization. Accordingly, various separation methods have been suggested. For example, low-purity 2,6-NDA produced by oxidization in a liquid phase is esterified with methanol (Japanese Unexamined Patent Application Publication No. 50-95253), and is subsequently distilled (Japanese Unexamined Patent Application Publication No. 50-29291) or recrystallized (Japanese Unexamined Patent Application Publication No. 50-111056) to prepare dimethyl 2,6-naphthalenedicarboxylate, which is a methyl ester. Then, the methyl ester is purified. In another method, crude 2,6-NDA is dissolved in an alkaline aqueous solution and is then decolorized (Japanese Unexamined Patent Application Publication Nos. 52-20993 and 52-20994, Japanese Examined Patent Application Publication Nos. 49-133359, 50-105639, 62-212341, and 62-212342), oxidized (Japanese Unexamined Patent Application Publication Nos. 48-68554, 48-68555, and 62-250849), or hydrogenated (Japanese Examined Patent Application Publication No. 57-36901).

In one of the above-described purification methods in which the methyl ester is purified, the carboxylic acid must be esterified with methanol in advance. This makes the purification process complex, and consequently the manufacturing cost increases. Also, in the other methods in which an alkali or an acid is used, purification equipment is readily corroded and separation of the acid or neutralization is required after the purification. Accordingly, these methods make aftertreatment complex and are, therefore, not cost effective.

Japanese Unexamined Patent Application Publication No. 9-151162 discloses that crude 2,6-NDA is reduced with hydrogen in the presence of a hydrogenation catalyst and is subsequently washed with a lower aliphatic carboxylic acid. In this method, the impurity FNA is reduced to 2-naphthoic acid (2-NA) with hydrogen, and then the naphthoic acid and methylnaphthoic acid (MNA) produced due to incomplete reduction are dissolved in a lower aliphatic carboxylic acid and then removed.

Unfortunately, this method needs a large amount of acid in the cleaning process, consequently causing the acid to corrode the equipment.

SUMMARY OF THE INVENTION

Accordingly, an object of the present invention is to provide a method for purifying crude 2,6-naphthalenedicarboxylic acid to produce high-purity 2,6-naphthalenedicarboxylic acid without damaging the equipment or increasing the cost, and making the purification process less complex.

The present invention is directed a method for purifying crude 2,6-naphthalenedicarboxylic acid including: a reduction step of reducing crude 2,6-naphthalenedicarboxylic acid containing 6-formyl-2-naphthoic acid with hydrogen to prepare a reduction product; and a cleaning step of cleaning the reduction product with alcohol.

Preferably, the reduction step includes a sub step of bringing the crude 2,6-naphthalenedicarboxylic acid and the hydrogen into contact with a hydrogenation catalyst in a liquid phase. Preferably, the liquid phase medium is water. The method may further include a dissolving step of dissolving the crude 2,6-naphthalenedicarboxylic acid and the hydrogen in the water. The dissolving step is performed before the reduction step. Preferably, the hydrogen concentration in the water is in the range of 10 to 100 ppm.

Preferably, the mass of the alcohol is in the range of 2 to 20 times the mass of the reduction product. Preferably, the alcohol is ethanol.

DESCRIPTION OF THE PREFERRED EMBODIMENTS

Figure 1:
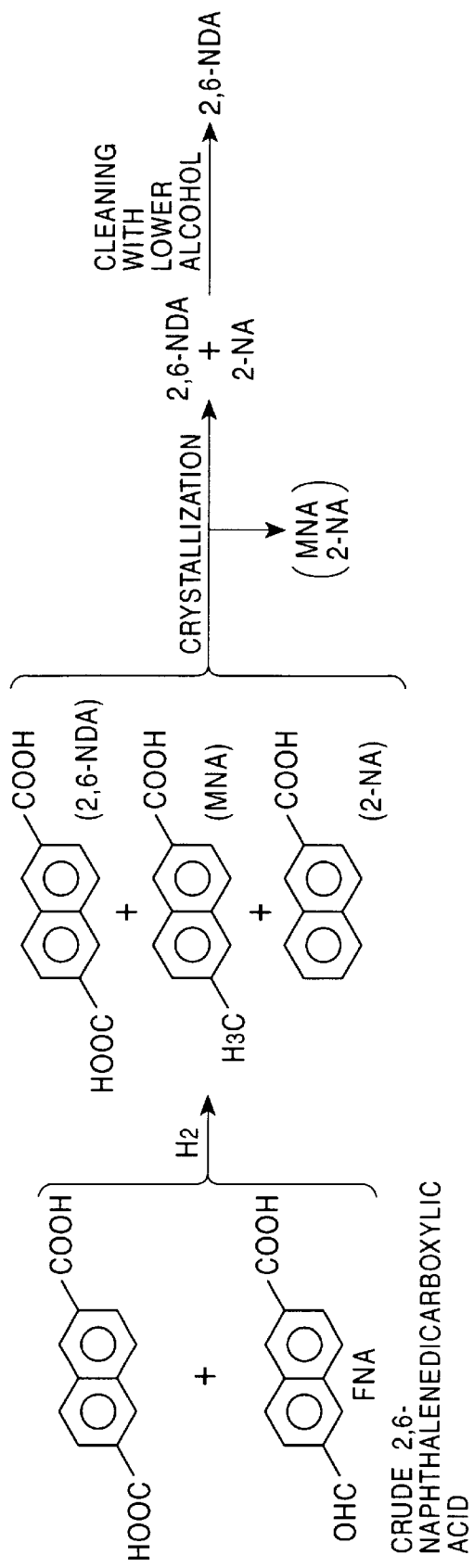
FIG. 1 is a flow diagram showing a method for purifying 2,6-naphthalenedicarboxylic acid of the present invention.

A method for purifying 2,6-NDA of the present invention will now be described with reference to FIG. 1.

Crude 2,6-naphthalenedicarboxylic acid (2,6-NDA), which is used as a material of the present invention, is generally produced from 2,6-dimethylnaphthalene (2,6-DMN) by oxidization and contains 6-formyl-2-naphthoic acid (FNA) as an impurity. In general, the content of the FNA in the 2,6-NDA is about 0.1 to 1.0 mass % although this depends on the method for producing 2,6-NDA.

The crude 2,6-NDA produced from 2,6-DMN by oxidization also contains other impurities such as a catalyst residue. Preferably, these impurities are removed by cleaning with acetic acid in advance.

The crude 2,6-NDA is reduced with hydrogen in the presence of a hydrogenation catalyst.

The hydrogenation catalyst is at least one noble metal selected from the group consisting of palladium, rhodium, ruthenium, osmium, iridium, and platinum, which belong to group VIII in the periodic table of elements. Preferably, the hydrogenation catalyst is selected from among palladium, rhodium, ruthenium, and platinum, and more preferably it is palladium. Preferably, such a noble metal catalyst is supported on a carrier. Exemplary carriers include activated carbon, graphite, alumina, zeolite, and silica. Activated carbon is inexpensive and has a large pore surface area and, therefore, it is advantageously used as the carrier.

Hydrogen gas may be diluted with a gas medium or a liquid medium to be supplied. Preferably, it is diluted with a liquid medium, and more preferably with water. This is because the reduction reaction with hydrogen efficiently proceeds in a homogeneous system in which hydrogen and 2,6-NDA are dissolved in comparison with in a three-phase system including a gas phase, a liquid phase, and a solid phase. Also, in the three-phase system, excess hydrogen gas must be recovered and a control system for the recovery is needed, and thus the purification system becomes complex. In contrast, the homogeneous liquid-phase system allows the aftertreatment to be simple and reduces the corrosion of the reactor.

If hydrogen gas is dissolved in water to be supplied, preferably, the hydrogen concentration in the aqueous solution is in the range of 10 to 100 ppm. A hydrogen content of less than 10 ppm cannot completely carry out the hydrogen reduction, and more than 100 ppm of hydrogen is likely to produce by-products due to excess hydrogen.

Since crude 2,6-NDA is solid at room temperature, preferably, it is dissolved in a liquid medium and is subsequently reduced with hydrogen in high-temperature water. In this instance, preferably, the content of crude 2,6-NDA in the water supplied for the reduction reaction is in the range of 5 to 30 mass %. It is preferable that the crude 2,6-NDA is dissolved in high-temperature water and that the hydrogen used for the reduction reaction is dissolved in water because the water serving as a liquid medium for the hydrogen can double as a solvent for the crude 2,6-NDA. In this instance, water containing hydrogen and water containing the crude 2,6-NDA may be mixed and brought into contact with the reduction catalyst, or hydrogen gas may be dissolved in the water containing the 2,6-NDA.

When the crude 2,6-NDA and the hydrogen are brought into contact with the hydrogenation catalyst in a liquid phase, any contacting method can be used, but it is preferable to use a method in which a solution containing crude 2,6-NDA and hydrogen is allowed to pass through a fixed-bed reactor packed with the hydrogenation catalyst, from the viewpoint of cost and maintainability.

Preferably, the reduction reaction is performed at a temperature in the range of 280 to 350° C. This is because 2,6-NDA is slightly soluble or insoluble in water at room temperature and it cannot be dissolved in water at a sufficient amount for the liquid phase reaction unless the water temperature is high. In addition, in order to maintain the liquid phase at a high temperature in the range described above, the pressure must be the saturated vapor pressure or higher (150 to 250 atm). Fortunately, using hydrogen dissolved in water prevents the equipment from deteriorating. Specifically, if hydrogen gas is supplied to a water medium containing 2,6-NDA, the hydrogen gas is used at such a high temperature and high pressure, consequently making the reactor brittle. In order to prevent the embrittlement, pressure-resistant equipment, which is expensive, is required.

Preferably, the hydrogen reduction is performed under the condition in which the weight hourly space velocity (WHSV) of a reaction solution containing hydrogen and 2,6-NDA is in the range of 12 to 200 $hr^{-1}$ for 1 g of a hydrogenation catalyst. When a palladium catalyst is used, the residence time (1/WHSV) of the reaction solution coming into contact with the catalyst is 5 min or less and preferably 3 min or less. Preferably, the lower limit of the residence time is 0.3 min. This is because an excess residence time promotes reduction of 2,6-NDA, consequently reducing the yield of 2,6-NDA.

When the hydrogen reduction is performed in a liquid phase, the reduction product needs to be crystallized before being cleaned because it is present in the liquid phase. The crystallization can be accomplished by cooling with a coolant or under a reduced pressure. In either case, preferably the liquid phase is cooled slowly. Since the solubility of methylnaphthoic acid (MNA), which is produced by an incomplete hydrogen reduction reaction, in water at high temperature and high pressure is higher than that of 2,6-NDA, by precipitating the 2,6-NDA beforehand, most of the methylnaphthoic acid (MNA) and part of 2-NA can be removed.

The cleaning step with alcohol will now be described.

Lower alcohols having a carbon number of 1 to 5, such as methanol, ethanol, propanol, and butanol, are advantageously used for the cleaning step. These alcohols are inexpensive and they do not affect the equipment by, for example, corroding the equipment. Also, they allow the aftertreatment to be simple. In addition, since the lower alcohols have low boiling points, the resulting purified product can be easily dried. Preferably, ethanol is selected from the above-described lower alcohols because it is harmless and easily evaporates.

The alcohol cleaning step is performed at room temperature. In general, as the temperature becomes higher, the solubility in alcohol increases. An excessively high temperature increases the solubility of 2,6-NDA in alcohol, and accordingly the 2,6-NDA cannot be sufficiently purified and the yield thereof decreases. Also, such a high temperature allows the alcohol to evaporate.

Preferably, the mass of alcohol for the cleaning step is 2 to 20 times that of the reduction product to be cleaned.

In order to clean the reduction product, the alcohol may be poured into the reduction product and, subsequently, the reduction product is subjected to suction filtration, or the alcohol and the reduction product contained together in an enclosure may be stirred. When the above-described amount of alcohol is used, preferably, the reduction product and the alcohol are stirred together for 5 to 60 min.

The solubility, in alcohol, of 2-NA, which is produced as an impurity by hydrogenation of 2,6-NDA, is higher than that of 2,6-NDA. Specifically, the solubility of 2-NA in alcohol is about 2 to 15 mass % at room temperature. While 10 mass % of 2-NA dissolves in ethanol, 2,6-NDA hardly dissolves in any alcohols. MNA also dissolves in alcohol. Therefore, by cleaning the reduction product with alcohol, impurities, that is, 2-NA and MNA, contained in the reduction product can be removed and thus the purity of the resulting 2,6-NDA can be increased.

After the alcohol cleaning step, another cleaning step with ion-exchanged water may be performed, but it is not necessary and only a drying step may follow when a volatile alcohol, which has a low boiling point, is used.

The reduction product is dried to obtain high-purity 2,6-NDA hardly containing any impurities. The resulting 2,6-NDA has a purity of 99.7% or more.

Figure 2:
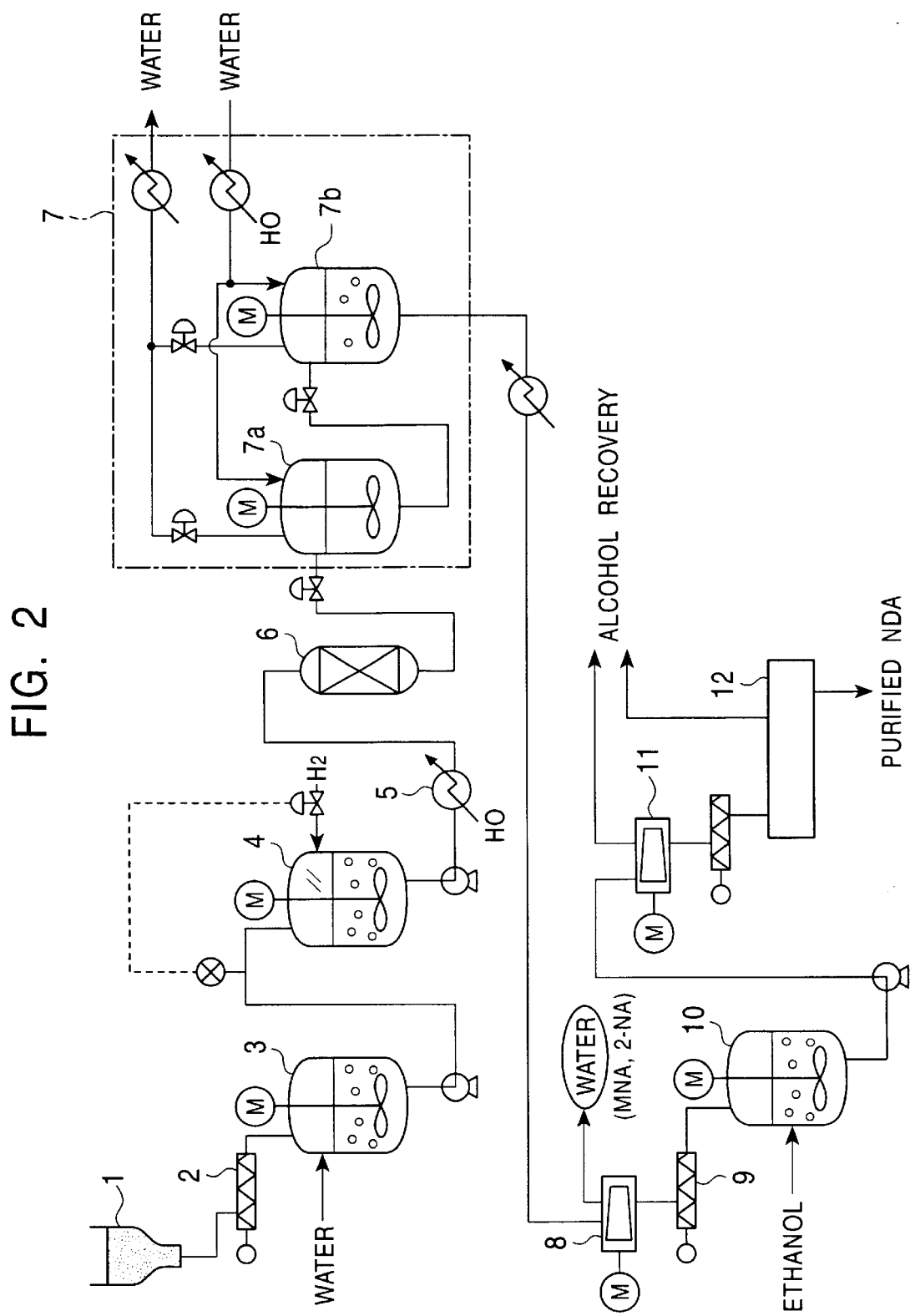
FIG. 2 is a schematic illustration of a system for the method of the present invention.

A purification system for the method of the present invention will now be described with reference to FIG. 2.

A predetermined amount of crude 2,6-NDA is introduced from a hopper 1 into a first mixer 3 via a feeder 2. The amount of crude 2,6-NDA is such that the 2,6-NDA can dissolve completely at a temperature at which it is subjected to hydrogen reduction. The first mixer 3 contains water and stirs the introduced crude 2,6-NDA to prepare a crude 2,6-NDA slurry. The slurry is introduced into a second mixer 4 and, simultaneously, compressed hydrogen gas is injected into the second mixer 4 to be dissolved in the water. In this instance, preferably, the pressure of the hydrogen gas is in the range of 5 to 100 atm. The slurry, which contains the hydrogen and the crude 2,6-NDA, is heated to a temperature of about 280 to 350° C. with a heat exchanger 5. Thus, 5 to 30 mass % of 2,6-NDA is dissolved. The heated solution is introduced into a reactor 6. The reactor 6 is packed with a hydrogenation catalyst, and the solution containing the hydrogen and the crude 2,6-NDA is introduced into the reactor 6. While passing through the reactor 6, the solution comes into contact with the hydrogenation catalyst so that the hydrogen reduction is induced. Since the hydrogen and the crude 2,6-NDA are dissolved in the water in the reactor 6, the reduction reaction can proceed uniformly. Also, since high-temperature hydrogen gas is not present in the reactor 6, the reactor 6 is hardly corroded.

The reduction product is gradually cooled down under a reduced pressure by a multistep thermal-insulated flashing apparatus 7. The thermal-insulated flashing apparatus shown in FIG. 2 is composed of two pressure-reducing vessels 7a and 7b, and a three-step or more flashing apparatus may also be used. Since water is evaporated by a reduced pressure, water is supplied to the pressure-reducing vessels accordingly so that rapid crystallization caused by a shortage of water is prevented. Slow crystallization allows 2-NA and 2,6-NDA to be present in the liquid phase and to increase the content of 2,6-NDA in a crystallized solid phase.

Slurry obtained by cooling is subjected to solid-liquid separation with a centrifuge 8. The solid-liquid separation may be conducted under an increased pressure. The liquid phase contains MNA and 2-NA, which have high solubility in water, and the solid phase contains 2,6-NDA at a high concentration. However, the solid phase still contains a small amount of 2-NA at this stage.

Next, a predetermined amount of the solid phase, which has been obtained by the separation, is placed in a washer 10 using a feeder 9. The washer 10 contains ethanol. The solid phase is stirred to allow mixing mixed with the ethanol in the washer 10, and is then subjected to solid-liquid separation with a centrifuge 11. The ethanol is recovered and the resulting purified 2,6-NDA is dried in a drier 12. The drier 12 may be a fluidized-bed type, a transverse-stirring type, or a kiln type. When a volatile alcohol such as ethanol is used as the cleaning agent, the purified 2,6-NDA may be dried in an airflow of nitrogen or under a reduced pressure.

The method for purifying 2,6-NDA of the present invention does not need aftertreatment of the agents (alcohol, hydrogen gas, and the reaction medium) used therein. Since these agents do not have factors which corrode the purification system, the method does not require expensive corrosion-resistant equipment.

EXAMPLES

Examples according to the method of the present invention will now be described.

The following two materials having compositions shown in Table 1 are used as crude 2,6-NDA

TABLE 1

| Crude 2,6-NDA | A | B |
|---|---|---|
| 2,6-NDA | 96.0 mass % | 97.0 mass % |
| FNA | 4400 ppm | 10260 ppm |

Example 1

Figure 3:
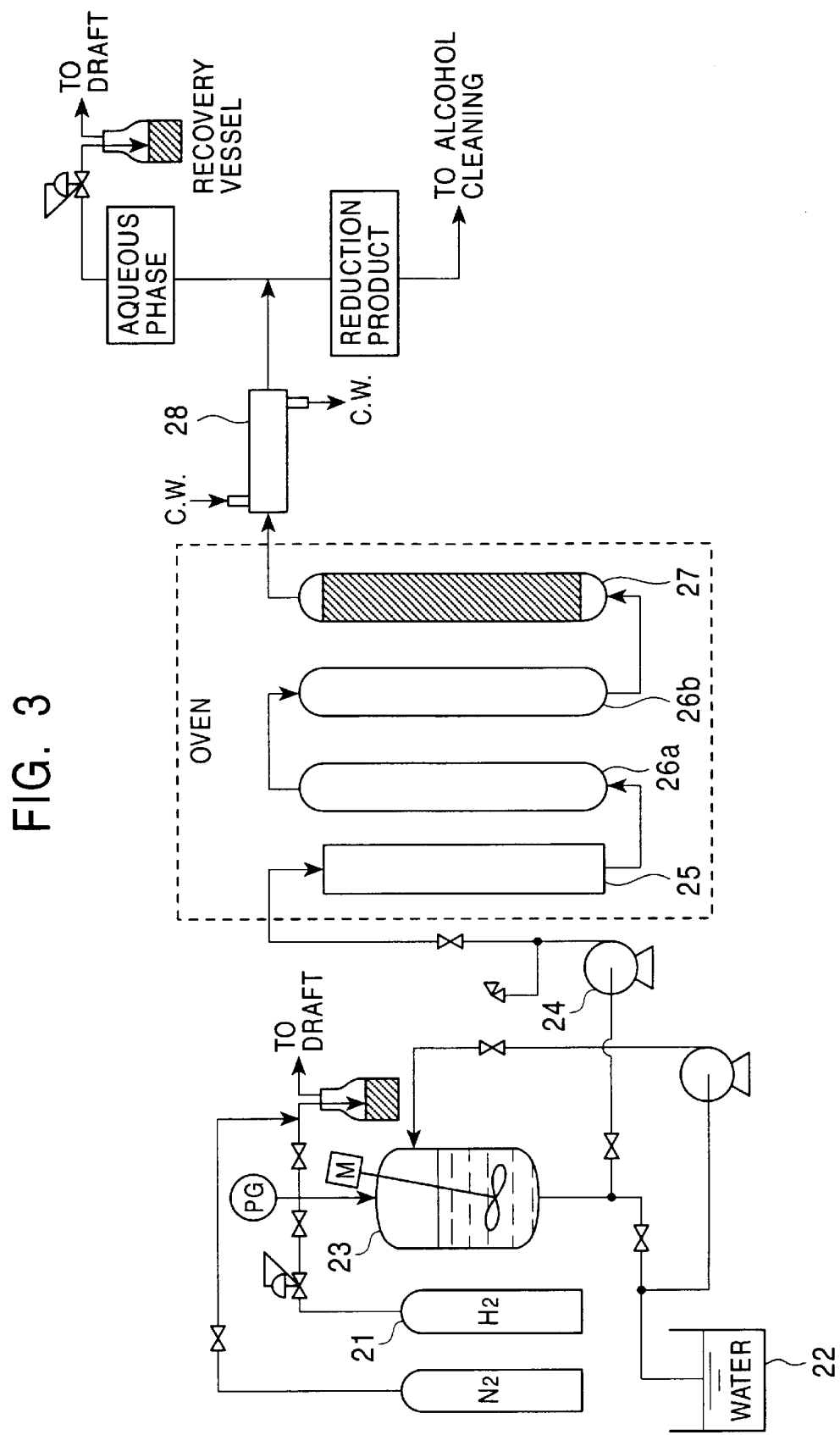
FIG. 3 is a schematic illustration of a system according to an embodiment of the present invention.

Hydrogen reduction was performed with a system shown in FIG. 3.

Specifically, 5 MPa hydrogen gas from a hydrogen gas cylinder 21 and water from a water bath 22 were supplied to a mixer 23 and stirred to dissolve the hydrogen gas in the water. In order to reduce the consumption of the hydrogen gas, nitrogen gas was introduced via a hydrogen-gas supplying line to replace air with the nitrogen gas before the hydrogen gas was introduced into the mixer 23.

The hydrogen solution was exposed to a heater 25 with a pump 24 and was heated to 330° C. The heated hydrogen solution was sent to a first vessel 26a and a second vessel 26b. The first vessel 26a and the second vessel 26b contained crude 2,6-NDA powder. By allowing the heated hydrogen solution to pass through the vessels 26a and 26b, part of the crude 2,6-NDA was dissolved in the heated solution.

The heated solution in which hydrogen and the crude 2,6-NDA were dissolved was subsequently sent to a reactor 27. The concentration of hydrogen in the supplied solution was 80 ppm. The reactor 27 was packed with 5.2 g of hydrogenation catalyst (activated carbon supporting 2 to 3 mass % of palladium). While the heated solution, in which the hydrogen and the crude 2,6-NDA were dissolved, passes through the reactor 27, the FNA contained as an impurity in the crude 2,6-NDA is reduced with the hydrogen. The pressure in the reactor 27 was 25 MPa. The weight hourly space velocity (WHSV) of the reaction solution was 11.5 $hr^{-1}$ with respect to the weight of the catalyst and the residence time of the reaction solution coming into contact with the catalyst was 5.2 min.

After passing through the reactor 27, the reaction liquid was cooled down in a cooler 28 at a high pressure of 15 MPa and was subsequently subjected to solid-liquid separation. The aqueous phase was recovered and the separated reduction product was subjected to composition analysis by high performance liquid chromatography. (HPLC).

Then, the reduction product was added to a mass of ethanol 5 times the mass thereof and was stirred with a magnetic stirrer at room temperature for 10 min. Then, the reduction product was subjected to suction filtration for solid-liquid separation. While undergoing suction, the solid which was separated out was subjected to cleaning with an amount of ethanol twice the amount of the solid and was successively washed with a large amount of ion-exchanged water. The solid was dried at 105° C. for 3 hours, and was then subjected to composition analysis by HPLC.

The results are shown in Table 2 with purification conditions.

Examples 2 to 6

Crude 2,6-NDA was purified as in Example 1 except that crude 2,6-NDA, the amount of alcohol for cleaning, or conditions for hydrogen reduction were changed according to Table 2. Table 2 shows the results of the composition analysis of samples obtained after the hydrogen reduction and after the alcohol cleaning. N.D. in Table 2 represents that the concentration of the corresponding substance is below the detection limit (20 ppm).

TABLE 2

| | No. | 1 | 2 | 3 | 4 | 5 | 6 |
|---|---|---|---|---|---|---|---|
| Crude 2,6-NDA | | A | A | A | B | B | B |
| Reduction conditions | Temperature (° C.) | 330 | 330 | 310 | 330 | 330 | 330 |
| | Pressure (MPa) | 25 | 25 | 25 | 25 | 15 | 25 |
| | Supplied hydrogen conc. (ppm) | 80 | 80 | 80 | 80 | 80 | 80 |
| | Catalyst amount (g) | 5.2 | 3.0 | 3.0 | 15.1 | 14.1 | 14.6 |
| | WHSV (hr$^{-1}$) | 11.5 | 20 | 20 | 6.0 | 6.0 | 3.0 |
| | 1/WHSV (min) | 5.2 | 3.0 | 3.0 | 10.0 | 10.0 | 20.0 |
| Reduction product | 2,6-NDA (wt %) | 98.8 | 99.6 | 98.8 | 97.6 | 97.9 | 96.9 |
| | FNA (ppm) | N.D. | N.D. | N.D. | N.D. | N.D. | N.D. |
| | 2-NA (ppm) | 13410 | 3640 | 9150 | 22400 | 18080 | 29800 |
| Ethanol amount (times) | | 7 | 7 | 7 | 12 | 12 | 12 |
| Composition after cleaning | 26-NDA (wt %) | 99.8 | 99.9 | 99.7 | 99.8 | 99.9 | 99.9 |
| | 2-NA (ppm) | 1200 | 1200 | 1400 | 620 | 600 | 680 |

As shown in Table 2, FNA was not detected in the crude 2,6-NDA after hydrogen reduction, and this suggests that the FNA was reduced to 2-NA. As the hydrogen reduction time became longer, the content of 2,6-NDA in the reduction product decreased, and this suggests that the 2,6-NDA was reducing. Therefore, in order to completely reduce FNA and to increase the yield of 2,6-NDA, preferably, the residence time (1/WHSV) of the reaction solution coming into contact with the catalyst is 3 min or less.

Table 2 also shows that the content of 2-NA decreased after the alcohol cleaning. Thus, the resulting 2,6-NDA had a purity of 99.7% or more.

Since the method of the present invention uses alcohol to remove FNA contained in the reduction product, the purification system is not corroded and treatment after the cleaning is simple.

Also, by performing the hydrogen reduction in an aqueous phase containing 2,6-NDA and hydrogen, deterioration of the reactor can be prevented.

What is claimed is:

1. A method for purifying crude 2,6-naphthalenedicarboxylic acid, comprising:
   reducing crude 2,6-naphthalenedicarboxylic acid containing 6-formyl-2-naphthoic acid with hydrogen and a hydrogenation catalyst comprising at least one noble metal selected from the group consisting of palladium, rhodium, ruthenium, osmium, iridium, and platinum to prepare a reduced 2,6-naphthalenedicarboxylic acid; and
   cleaning the reduced 2,6-naphthalenedicarboxylic acid with alcohol.

2. The method for purifying crude 2,6-naphthalnedicarboxylic acid according to claim 1, wherein the reducing is performed in a liquid phase.

3. The method for purifying crude 2,6-naphthalenedicarboxylic acid according to claim 2, wherein the liquid phase comprises water.

4. The method for purifying crude 2,6-naphthalenedicarboxylic acid according to claim 3, further comprising dissolving the crude 2,6 naphthalenedicarboxylic acid and the hydrogen in the Water before the reducing.

5. The method for purifying crude 2,6-naphthalenedicarboxylic acid according to claim 3, wherein the hydrogen concentration in the water is in the range of 10 to 100 ppm.

6. The method for purifying crude 2,6-naphthalenedicarboxylic acid according to claim 1, wherein the mass of the alcohol is in the range of 2 to 20 times the mass of the reduction product.

7. The method for purifying crude 2,6-naphthalenedicarboxylic acid according to claim 1, wherein the alcohol is ethanol.

8. The method for purifying crude 2,6-napthalenedicarboxylic acid according to claim 1, further comprising recovering the purified 2,6-napthalenedicarboxylic acid.

9. In a method of producing a plastic, the improvement comprising purifying crude 2,6-napthalenedicarboxylic acid according to claim 1.

10. In a method of producing a plastic comprising one or both of polyethylene napthalate and polybutylene napthalate, the improvement comprising purifying crude 2,6-napthalenedicarboxylic acid according to claim 1.

11. In a method of producing a plastic, the improvement comprising purifying crude 2,6-napthalenedicarboxylic acid according to claim 4.

12. In a method of producing a plastic comprising one or both of polyethylene napthalate and polybutylene napthalate, the improvement comprising purifying crude 2,6-napthalenedicarboxylic acid according to claim 4.

13. In a method of producing a plastic, the improvement comprising purifying crude 2,6-napthalenedicarboxylic acid according to claim 5.

14. In a method of producing a plastic comprising one or both of polyethylene napthalate and polybutylene napthalate, the improvement comprising purifying crude 2,6-napthalenedicarboxylic acid according to claim 5.

15. In a method of producing a plastic, the improvement comprising purifying crude 2,6-napthalenedicarboxylic acid according to claim 6.

16. In a method of producing a plastic comprising one or both of polyethylene napthalate and polybutylene napthalate, the improvement comprising purifying crude 2,6-napthalenedicarboxylic acid according to claim 6.

17. In a method of producing a plastic, the improvement comprising purifying crude 2,6-napthalenedicarboxylic acid according to claim 7.

18. In a method of producing a plastic comprising one or both of polyethylene napthalate and polybutylene napthalate, the improvement comprising purifying crude 2,6-napthalenedicarboxylic acid according to claim 7.

19. In a method of producing a plastic, the improvement comprising purifying crude 2,6-napthalenedicarboxylic acid according to claim 8.

20. In a method of producing a plastic comprising one or both of polyethylene napthalate and polybutylene napthalate, the improvement comprising purifying crude 2,6-napthalenedicarboxylic acid according to claim 8.

* * * * *

UNITED STATES PATENT AND TRADEMARK OFFICE
CERTIFICATE OF CORRECTION

PATENT NO. : 6,756,509 B2
DATED : June 29, 2004
INVENTOR(S) : Nagase et al.

It is certified that error appears in the above-identified patent and that said Letters Patent is hereby corrected as shown below:

Title page,
Item [73], Assignee, should read:
-- [73] Kabushiki Kaisha Kobe Seiko Sho (Kobe Steel, Ltd.), Kobe (JP) --

Signed and Sealed this

Thirty-first Day of August, 2004

JON W. DUDAS
*Director of the United States Patent and Trademark Office*